(12) United States Patent
Eh

(10) Patent No.: US 7,064,102 B2
(45) Date of Patent: Jun. 20, 2006

(54) ALICYCLIC ESTERS HAVING A MUSKY SMELL

(75) Inventor: Marcus Eh, Holzminden (DE)

(73) Assignee: Symrise GmbH & Co, KG (DE)

( * ) Notice: Subject to any disclaimer, the term of this patent is extended or adjusted under 35 U.S.C. 154(b) by 0 days.

(21) Appl. No.: 10/510,024

(22) PCT Filed: Mar. 29, 2003

(86) PCT No.: PCT/EP03/03294

§ 371 (c)(1),
(2), (4) Date: Oct. 1, 2004

(87) PCT Pub. No.: WO03/082799

PCT Pub. Date: Oct. 9, 2003

(65) Prior Publication Data

US 2005/0182273 A1    Aug. 18, 2005

(51) Int. Cl.
*A61K 8/18*    (2006.01)
*C07C 69/66*    (2006.01)

(52) U.S. Cl. ........................................ 512/22; 560/188

(58) Field of Classification Search .................... None
See application file for complete search history.

(56) References Cited

U.S. PATENT DOCUMENTS 4,622,221 A * 11/1986 Schleppnik ................ 424/76.4
5,166,412 A * 11/1992 Giersch et al. ............. 560/231
RE38,659 E * 11/2004 Williams .................... 560/249

* cited by examiner

*Primary Examiner*—Paul A. Zucker
(74) *Attorney, Agent, or Firm*—Akerman Senterfitt; Stephen A. Pendorf

(57) ABSTRACT

The invention relates to novel alicyclic esters, methods for the their preparation, their use as fragrances and also perfumed products and fragrance mixtures containing the compounds according to the invention.

11 Claims, No Drawings

ALICYCLIC ESTERS HAVING A MUSKY SMELL

FIELD OF THE INVENTION

The invention relates to novel alicyclic esters, methods for their preparation, their use as fragrances, and also perfumed products and fragrance mixtures containing the compounds according to the invention.

BACKGROUND OF THE INVENTION

Compounds with a musk fragrance are sought-after components in the perfume industry. They are characterized both by their property of imparting an aura to perfume compositions and also by their ability to act as a fixer. Thus, musk fragrances are nowadays used in many perfume compositions.

The synthesis of biodegradable compounds with a musk fragrance has gained substantially in importance in recent years, since the synthetic musk compounds of the nitro-aromatic and polycyclic series are persistent and lipophilic, so that these compounds accumulate in aquatic food chains and fatty tissue (H. Brunn, G. Rimkus, Ernährungs-Umschau 1996, 43, 442 to 449; H. Brunn, G. Rimkus, Ernährungs-Umschau 1997, 44, 4 to 9). In order to close the gap, macrocyclic musk fragrances that are similar to natural compounds and are characterized by a macrocyclic ring with 13 to 17 C atoms, which has a ketone or an ester as functional group, have been developed to an increasing extent.

Furthermore, U.S. Pat. No. 5,166,412 discloses compounds of type (II)

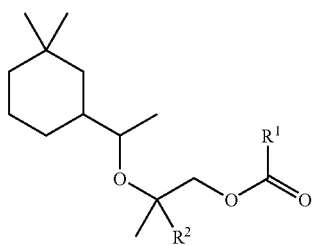

(II)

where $R^1$ is a $C_1$ to $C_3$ alkyl group and $R^2$ is an H or a methyl group. These compounds are characterized by a musk fragrance that is associated with ambergris and fruity aspects.

In addition, WO-A 00/14051 shows that esters of type (III)

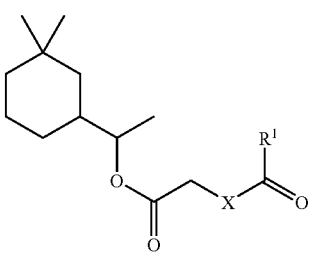

(III)

where $R^1$ is a $C_1$ to $C_4$ alkyl or alkylene group and X is an oxygen, a methylene or ethylene group, also have a musk fragrance, the ambergris and fruity aspects being further in the background.

The aim was now to find compounds which, on the one hand, have a musk fragrance and in addition, by means of further original fragrance aspects, expand the range of raw materials available for the composition of perfumes.

SUMMARY OF THE INVENTION

The present invention relates to novel alicyclic esters of the formula (I)

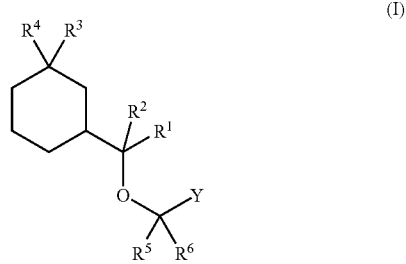

(I)

where $R^1=CH_3$, $R^3=H$ or $CH_3$ and $R^2$ and $R^4=H$, $R^5$ and $R^6$—independently of one another—are H or $CH_3$ and $Y=-CR^7R^8OCOR^9$, where $R^7$ and $R^8$—independently of one another—are H or $CH_3$ and $R^9$ is a branched or straight-chain $C_1$ to $C_5$ alkyl group or a branched or straight-chain $C_2$ to $C_5$ alkylene group, or $R^1$ and $R^2$—independently of one another—are $CH_3$ or $CH_2CH_3$, $R^3$ and $R^4$—independently of one another—are H or $CH_3$, $R^5$ and $R^6$ together are oxygen and $Y=-CR^7R^8OCOR^9$ or $R^9$, where $R^7$, $R^8$ and $R^9$ have the abovementioned meaning, or $R^1$ and $R^2$—independently of one another—are $CH_3$ or $CH_2CH_3$, $R^3$, $R^4$, $R^5$ and $R^6$—independently of one another—are H or $CH_3$ and $Y=-CR^7R^8OCOR^9$, where $R^7$, $R^8$ and $R^9$ have the abovementioned meaning.

The present invention also relates to methods for the preparation of the compounds according to the invention, their use as fragrances and also perfumed products and fragrance mixtures containing the compounds according to the invention.

DETAILED DESCRIPTION

According to the invention branched or straight-chain $C_1$ to $C_5$ alkyl groups are understood to be, in particular, the alkyl radicals methyl, ethyl, n-propyl, iso-propyl, n-butyl, sec.-butyl, iso-butyl, tert.-butyl, n-pentyl, iso-pentyl and 3-methylbutyl. The alkyl radicals methyl, ethyl, n-propyl, iso-propyl, n-butyl, sec.-butyl, and iso-butyl are preferred; the radicals methyl, ethyl and n-propyl are particularly preferred.

According to the invention branched or straight-chain $C_2$ to $C_5$ alkylene groups are understood to be in particular, the alkylene radicals ethenyl, methylethenyl, 1-propenyl, 2-propenyl, 2-methyl-1-propenyl, 1-methyl-1-propenyl, 1-butenyl, 3-butenyl, 1-methyl-1-butenyl, 1-methyl-3-butenyl, 3-methyl-3-butenyl, 1-pentenyl, 2-pentenyl, and 4-pentenyl. The alkylene radicals ethenyl, methylethenyl, 1-propenyl, 2-propenyl, 2-methyl-1-propenyl, and 1-methyl-1-propenyl are preferred; the alkylene radicals ethenyl, methylethenyl, and 1-propenyl are particularly preferred.

The novel alicyclic esters of the formula (I), according to the invention, can be in the optically active form and also in the form of arbitrary mixtures of their stereoisomers.

The alicyclic esters of the formula (I), according to the invention, achieve the stated objective; in addition to musk-like fragrance notes that are of interest from the perfume standpoint, they are characterized by interesting subsidiary notes. In this context it has been found, surprisingly, that the compounds in which $R^1$ and $R^2$ are methyl groups are characterized by very fine woody aspects in addition to the musk note. The woody aspects retreat completely into the background if $R^1$ is a methyl group and $R^2$, $R^3$, and $R^4$ are hydrogen, so that these compounds are characterized by flowery aspects, coupled with fruity accents.

Compounds that are particularly valuable from the sensory standpoint are compounds of the formula (IV), which have a tertiary alkoxy group ($R^1$, $R^2$=$CH_3$), since they also have woody aspects in addition to the musk note.

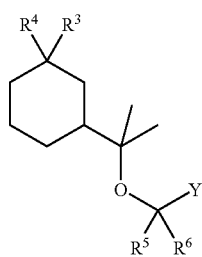

(IV)

where $R^3$ and $R^4$—independently of one another—are H or $CH_3$, where $R^3$ and $R^4$=methyl is preferred $R^5$ and $R^6$ together are hydrogen, and Y=—$CR^7R^8OCOR^9$ or $R^9$, where $R^7$, $R^8$, and $R^9$ have the abovementioned meaning, where Y=methyl, ethyl or n-propyl, and also Y=—$CR^7R^8OCOR^9$, where $R^7$ and $R^8$=H and $R^9$=methyl, ethyl or n-propyl is preferred.

The compound of the formula (V), where the sweet, erogenous musk fragrance is associated with soft, woody aspects in a unique manner, is particularly preferred, because of its attractive olfactory properties.

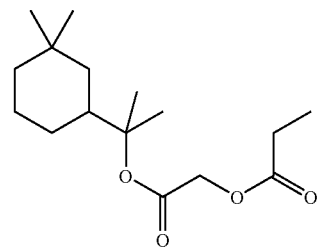

(V)

A further class of molecules that are very interesting from the sensory standpoint and that also have flowery and fruity aspects in addition to the musk note are represented in formula (VI).

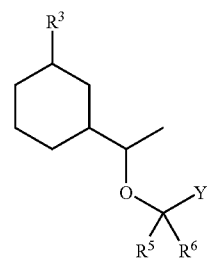

(VI)

where $R^3$=H or $CH_3$, $R^5$ and $R^6$—independently of one another—are H or $CH_3$, where $R^5$, $R^6$=methyl is preferred, and Y=—$CR^7R^8OCOR^9$, where $R^7$, $R^8$, and $R^9$ have the abovementioned meaning, where $R^7$ and $R^8$=H and $R^9$=methyl, ethyl or n-propyl is preferred.

The isomers of the formulae (VIIa) and (VIIb), where the erogenous, slightly ambergris-tinged musk fragrance is associated with intensive flowery aspects in a unique manner, are particularly preferred, because of their attractive olfactory properties.

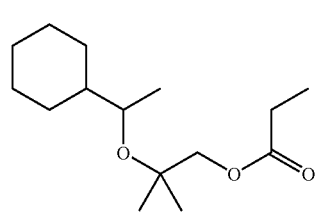

(VIIa)

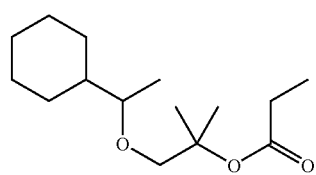

(VIIb)

In this context according to the invention, the alicyclic esters of the formula (I) can be used as individual substances in a multiplicity of products; particularly advantageous they can be combined with other fragrances to give novel perfume compositions.

According to the invention, by using the alicyclic esters of formula (I) it is as a rule possible, even in low dosage, to achieve fine, erogenous musk notes associated with woody or flowery aspects in the resulting perfume compositions, the overall fragrance impression being strikingly harmonized, the aura being discernably increased and fixing, i.e. the adhesion of the perfume oil, being distinctly increased.

According to the invention, examples of fragrances with which the alicyclic esters of the formula (I) can advantageously be combined as provided, for example, in K. Bauer, D. Garbe and H. Surburg, Common Fragrance and Flavor Materials, $3^{rd}$. Ed., Wiley-VCH, Weinheim 1997.

The following may be mentioned individually:

extracts from natural, raw materials, such as, essential oils, concretes, absolutes, resins, resinoids, balsams, tinctures, such as, for example, ambergris tincture; amyris oil; angelica seed oil; angelica root oil; aniseed oil; valerian oil; basil oil; wood moss absolute; bay oil; mugwort oil; benzoin resin; bergamot oil; beeswax absolute; birch tar oil; bitter almond oil; savory oil; bucho leaf oil; cabreuva oil; cade oil; calamus oil; camphor oil; cananga oil; cardamom oil; cascarilla oil; cassia oil; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; davana oil; dill herb oil; dill seed oil; eau de brouts absolute; oakmoss absolute; elemi oil; tarragon oil; eucalyptus citriodoura oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; camomile oil blue; Roman camomile oil; carrot seed oil; cascarilla oil; pine needle oil; spearmint oil; caraway oil; labdanum oil; labdanum absolute; ladanum resin; lavandin absolute; lavandin oil; lavender absolute; lavender oil; lemongrass oil; lovage oil; distilled lime oil; pressed lime oil; linaloe oil; litsea cubeba oil; bayleaf oil; mace oil; marjoram oil; mandarin oil; massoi bark oil; mimosa absolute; musk seed oil; musk tincture; clary oil; nutmeg oil; myrrh absolute; myrrh oil; myrtle oil; clove leaf oil; clove blossom oil; neroli oil; olibanum absolute; olibanum oil; opopanax oil; orange blossom absolute; orange oil; origanum oil; palmarosa oil; patchouli oil; perilla oil; Peruvian balsam oil; parsley leaf oil; parsley seed oil; petitgrain oil; peppermint oil; pepper oil; pimenta oil; pine oil; pennyroyal oil; rose absolute; rosewood oil; rose oil; rosemary oil; Dalmation sage oil; Spanish sage oil; sandalwood oil; celery seed oil; spike lavender oil; Japanese anise oil; styrax oil; tagetes oil; fir needle oil; tea tree oil; turpentine oil; thyme oil; Tolu balsam; tonka absolute; tuberose absolute; vanilla extract; violet leaf absolute; verbena oil; vetiver oil; juniper oil; wine lees oil; absinthe oil; wintergreen oil; ylang oil; hyssop oil; civet absolute; cinnamon leaf oil; cinnamon bark oil; and fractions thereof or constituents isolated therefrom;

individual fragrances from the group comprising the hydrocarbons, such as, for example, 3-carene; α-pinene; β-pinene; α-terpinene; γ-terpinene; p-cymene; bisabolene; camphene; caryophyllene; cedrene; famesene; limonene; longifolene; myrcene; ocimene; valencene; (E,Z)-1,3,5-undecatriene;

the aliphatic alcohols, such as, for example, hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; the aliphatic aldehydes and the 1,4-dioxacycloalken-2-ones thereof, such as, for example, hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; and citronellyloxyacetaldehyde;

the aliphatic ketones and oximes thereof, such as, for example, 2-heptanone; 2-octanone; 3-octanone; 2-nonanone; 5-methyl-3-heptanone; 5-methyl-3-heptanone oxime; 2,4,4,7-tetramethyl-6-octen-3-one; the aliphatic sulphur-containing compounds, such as, for example, 3-methylthiohexanol; 3-methylthiohexyl acetate; 3-mercaptohexanol; 3-mercaptohexyl acetate; 3-mercaptohexyl butyrate; 3-acetylthiohexyl acetate; and 1-menthene-8-thiol;

the aliphatic nitriles, such as, for example, 2-nonenoic acid nitrile; 2-tridecenoic acid nitrile; 2,12-tridecenoic acid nitrile; 3,7-dimethyl-2,6-octadienoic acid nitrile; and 3,7-dimethyl-6-octenoic acid nitrile;

the aliphatic carboxylic acids and esters thereof, such as, for example, (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynoate; methyl 2-nonynoate; allyl 2-isoamyloxyacetate; and methyl 3,7-dimethyl-2,6-octadienoate;

the acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, and 3-methyl-2-butenoates thereof;

the acyclic terpene aldehydes and ketones, such as, for example, geranial; Neral; cirtonellal; 7-hydroxy-3,7-dimethyloctanal; 7-methoxy-3,7-dimethyl-octanal; 2,6,10-trimethyl-9-undecenal; geranylacetone; and the dimethyl and diethyl acetals of geranial, Neral, and 7-hydroxy-3,7-dimethyloctanal;

the cyclic terpene alcohols, such as, for example, menthol; isopulegol; alpha-terpineol; terpineol-4; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates, and 3-methyl-2-butenoates thereof;

the cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; deltadamascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal, and acetylated cedarwood oil (methyl cedryl ketone);

the cyclic alcohols, such as, for example, 4-tert-butylcyclohexanol; 3,3,5-trimethylcyclohexanol; 3-isocamphylcyclohexanol; and 2,6,9-trimethyl-Z2,Z5,E9-cyclo-dodecatrien-1-ol and 2-isobutyl-4-methyltetrahydro-2H-pyran-4-ol;

the cycloaliphatic alcohols, such as, for example, alpha-3,3-trimethyl-cyclohexyl-methanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol, and 1-(2,2,6-trimethylcyclo-hexyl)hexan-3-ol;

the cyclic and cycloaliphatic ethers, such as, for example, cineole; cedryl methyl ether; cyclododecyl methyl ether; (ethoxymethoxy) cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1b]furan; 1,5,9-trimethyl-13-oxabicyclo[10.1.0]trideca-4,8-diene; and rose oxide and 2-(2,4-dimethyl-3-cyclohexen-1-yl)-5-methyl-5-(1-methylpropyl)-1,3-dioxane;

the cyclic ketones, such as, for example, 4-tert-butylcyclohexanone; 2,2,5-trimethyl-5-pentylcyclopentanone; 2-heptylcyclopentanone; 2-pentylcyclo-pentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert-pentylcyclohexanone; 5-cyclohexadecen-1-one; 6,7-dihydro-1,1,2,3,3-pentamethyl-4(5H)-indanone; 5-cyclohexadecen-1-one; 8-cyclohexadecen-1-one; 9-cycloheptadecen-1-one and cyclo-pentadecanone;

the cycloaliphatic aldehydes, such as, for example, 2,4-dimethyl-3-cyclo-hexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde, and 4-(4-methyl-3-penten-1-yl)-3-cyclohexenecarbaldehyde;

the cycloaliphatic ketones, such as, for example, 1-(3,3-dimethylcyclo-hexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone, and tert-butyl 2,4-dimethyl-3-cyclohexen-1-yl ketone;

the esters of cyclic alcohols, such as, for example, 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetra-hydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate, and 4,7-methanooctahydro-5 or 6-indenyl acetate;

the esters of cycloaliphatic carboxylic acids, such as, for example, allyl 3-cyclohexylpropionate; allyl cyclohexyloxyacetate; methyl dihydrojasmonate; methyl jasmonate; methyl 2-hexyl-3-oxocyclopentanecarboxylate; ethyl 2-ethyl-6,6-dimethyl-2-cyclo-hexenecarboxylate; ethyl 2,3,6,6-tetramethyl-2-cyclohexenecarboxylate, and ethyl 2-methyl-1,3-dioxolane-2-acetate;

the aromatic hydrocarbons, such as, for example, styrene and diphenylmethane;

the araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol, and 1-(4-isopropylphenyl) ethanol;

the esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; the araliphatic ethers, such as, for example, 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropic aldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; and 4,4a,5,9b-tetrahydro-2,4-dimethylindeno[1,2-d]-m-dioxin;

the aromatic and araliphatic aldehydes, such as, for example, benzaldehyde; phenylacetaldehyde; 3-phenylpropanal; hydratropic aldehyde; 4-methylbenzaldehyde; 4-methylphenylacetaldehyde; 3-(4-ethylphenyl)-2,2-dimethylpropanal; 2-methyl-3-(4-isopropyl-phenyl)propanal; 2-methyl-3-(4-tert-butylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxy-benzaldehyde; 4-hydroxy-3-ethoxy-benzaldehyde; 3,4-methylenedioxy-benzaldehyde; 3,4-dimethoxybenzaldehyde; 2-methyl-3-(4-methoxy-phenyl) propanal and 2-methyl-3-(4-methylenedioxyphenyl) propanal;

the aromatic and araliphatic ketones, such as, for example, acetophenone; 4-methylacetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; and 1-[2,3-dihydro-1,1,2,6-tetramethyl-3-(1-methylethyl)-1H-5-indenyl]ethanone and 5',6',7',8'-tetrahydro-3',5',5',6',8',8'-hexamethyl-2-acetonaphthone;

the aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl 3-phenylglycidate and ethyl 3-methyl-3-phenylglycidate;

the nitrogen-containing aromatic compounds, such as, for example, 2,4,6-trinitro-1,3-dimethyl-5-tert-butylbenzene;

3,5-dinitro-2,6-dimethyl-4-tert-butylacetophenone; cinnamonitrile; 5-phenyl-3-methyl-2-pentenoic acid nitrile; 5-phenyl-3-methylpentanoic acid nitrile; methyl anthranilate; methyl N-methylanthranilate; Schiffs bases of methyl anthranilate with 7-hydroxy-3,7-dimethyloctanal; 2-methyl-3-(4-tert-butylphenyl)propanal or 2,4-dimethyl-3-cyclohexenecarbaldehyde; 6-isopropylquinoline; 6-isobutylquinoline; 6-sec-butylquinoline; indole; scatole; and 2-methoxy-3-isopropylpyrazine and 2-isobutyl-3-methoxypyrazine;

the phenols, phenyl ethers and phenyl esters, such as, for example, estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; and 2-ethoxy-5-(1-propenyl)phenol and p-cresyl phenylacetate;

the heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one and 2-ethyl-3-hydroxy-4H-pyran-4-one;

the lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin and octahydrocoumarin.

According to the invention, the perfume oils containing the alicyclic esters of the formula (I) according to the invention can be used in liquid form, undiluted or diluted, with a solvent for perfuming purposes. Suitable solvents for this purpose are, for example, ethanol, isopropanol, diethylene glycol monoethyl ether, glycerol, propylene glycol, 1,2-butylene glycol, dipropylene glycol, diethyl phthalate, triethyl citrate, isopropyl myristate, etc.

Furthermore, according to the invention, the perfume oils containing the alicyclic esters of the formula (I) can be adsorbed on a carrier, which serves both for fine dispersion of the fragrances in the product and, also, for controlled release during use. Such carriers can be porous inorganic materials, such as light sulphate, silica gels, zeolites, gypsums, clays, clay granules, gas concrete, etc. or organic materials, such as woods and cellulose-based substances.

According to the invention, the perfume oils containing the alicyclic esters of the formula (I) according to the invention can also be microencapsulated, spray-dried, in the form of inclusion complexes or in the form of extrusion products and can be added in this form to the product to be perfumed.

The properties of the perfume oils modified in this way can optionally be further optimised by so-called, "coating" with suitable materials with regard to a more targeted fragrance release, for which purpose waxy plastics, such as, for example, polyvinyl alcohol, are preferably used.

The microencapsulation of the perfume oils can, for example, be carried out by the so-called coacervation method, with the aid of capsule materials made from, for example, polyurethane-like substances or soft gelatine. The spray-dried perfume oils can, for example, be prepared by spray drying an emulsion or dispersion containing the perfume oil, where the carriers used can be modified starches, proteins, dextrin, and vegetable gums. Inclusion complexes can be prepared, for example, by introducing dispersions of the perfume oil and cyclodextrins or urea derivatives into a suitable solvent, e.g. water. Extrusion products can be obtained by melting the perfume oils with a suitable waxy substance and by extrusion with subsequent solidification, optionally, in a suitable solvent, e.g. isopropanol.

According to the invention, in perfume compositions, the amount of the alicyclic esters of the formula (I) that is used is 0.05 to 50% (m/m), preferably 0.5 to 20% (m/m), based on the total perfume oil.

According to the invention, the perfume oils containing the alicyclic esters of the formula (I) according to the invention can be used in concentrated form, in solutions, or in a modified form described above for the preparation of, for example, perfume extracts, eau de parfums, eau de toilettes, aftershaves, eau de colognes, pre-shave products, splash colognes, perfumed freshening wipes and for perfuming acid, alkaline, and neutral cleaning agents, such as, for example, floor cleaners, window cleaners, washing-up liquids, bath and sanitary equipment cleaners, scouring agents, solid and liquid WC cleaners, carpet cleaners in powder and foam form, liquid detergents, powder detergents, laundry pre-treatment agents, such as bleaching agents, softeners and stain removers, fabric conditioners, laundry soaps, laundry tablets, disinfectants, surface disinfectants and air fresheners in liquid or gel form or applied to a solid support, aerosol sprays, waxes and polishes, such as furniture polishes, floor waxes, cream shoe polishes and personal hygiene agents, such as, for example, solid and liquid soaps, shower gels, shampoos, shaving soaps, shaving foams, bath oils, cosmetic emulsions of the oil-in-water, of the water-in-oil and of the water-in-oil-in-water type, such as, for example, skin creams and lotions, face creams and lotions, sun protection creams and lotions, after-sun creams and lotions, hand creams and lotions, foot creams and lotions, depilatory creams and lotions, after-shave creams and lotions, bronzing creams and lotions, hair care products, such as, for example, hair sprays, hair gels, hair lotions, hair rinses, permanent and semi-permanent hair dyes, hair shaping agents such as cold permanent waves, and hair smoothing agents, hair tonics, hair creams and lotions, deodorants and antiperspirants, such as, for example, under-arm sprays, roll-ons, deodorants sticks, deodorant creams or decorative cosmetic products, such as, for example, eye shadows, nail varnishes, make-ups, lipsticks and mascara, and also of candles, lamp oils, fumigating sticks, insecticides, repellents, and propellants.

According to the invention, the novel alicyclic esters can, for example, be prepared in the following way:

The preparation of the alicyclic esters of the formula (1), according to the invention, in which:

$R^1$ and $R^2$—independently of one another—are $CH_3$ or $CH_2CH_3$, $R^3$ and $R^4$—independently of one another—are H or $CH_3$, $R^5$ and $R^6$ together are oxygen, and Y is —$CR^7R^8OCOR^9$, where $R^7$ and $R^8$—independently of one another—are H or $CH_3$ and $R^9$ is a branched or straight-chain $C_1$ to $C_5$ alkyl group or a branched or straight-chain $C_2$ to $C_5$ alkylene group can be carried out in accordance with synthesis route A.

In synthesis route A, the substituted cyclohexylalkanol (VIII) is esterified with the carboxylic acid (IX), which is obtainable by reaction of the corresponding α-hydroxycarboxylic acid with the corresponding acid chloride (Thayer, F. K., Organic Synthesis Col. Vol. 1 (1932), p. 12). The esterification can be carried out by methods well known to those skilled in the art, for example, by heating the two educts in a water separator in the presence of an entraining agent (for example toluene or cyclohexane) with the addition of 0.01% (mol) to 10% (mol), preferably 0.1% (mol) to 5% (mol), of an acid, preferably p-toluenesulphonic acid or sulphuric acid, or by the so-called Steglich method, where the esterification is carried out with the addition of dicyclohexylcarbodiimide and 0.02% (mol) to 20% (mol), preferably 0.5% (mol) to 10% (mol) 4-dimethylaminopyridine.

The preparation of the alicyclic esters of the formula (I) according to the invention in which $R^1$ and $R^2$—independently of one another—are $CH_3$ or $CH_2CH_3$, $R^3$ and $R^4$—independently of one another—are H or $CH_3$, $R^5$ and $R^6$ together are oxygen and $Y=R^9$ and $R^9$ has the abovementioned meaning, can be carried out in accordance with synthesis route B.

In synthesis route B, the substituted cyclohexylalkanol (VIII) is esterified by the methods well known to those skilled in the art. Here, the esterification can take place by heating the substituted cyclohexylalkanol (VIII) and the corresponding carboxylic acid in a water separator, in the presence of an entraining agent (for example, toluene or cyclohexane) with the addition of 0.01% (mol) to 10% (mol), preferably 0.1% (mol) to 5% (mol) of an acid, preferably, p-toluenesulphonic acid or sulphuric acid, or by reaction of the substituted cyclohexylalkanol (VIII) with the corresponding carboxylic acid anhydride in the presence of triethylamine and 0.5% (mol) to 50% (mol), preferably 1.0% (mol) to 30% (mol), 4-dimethyl-aminopyridine.

The preparation of the alicyclic esters of the formula (I) according to the invention in which $R^1=CH_3$, $R^3=H$ or $CH_3$ and $R^2$ and $R^4=H$, $R^5$ and $R^6$—independently of one another—are H or $CH_3$ and $Y=-CR^7R^8OCOR^9$, where $R^7$, $R^8$ and $R^9$ have the abovementioned meaning, or $R^1$ and $R^2$—independently of one another—are $CH_3$ or $CH_2CH_3$, $R^3$, $R^4$, $R^5$ and $R^6$—independently of one another—are H or $CH_3$ and $Y=-CR^7R^8OCOR^9$, where $R^7$, $R^8$ and $R^9$ have the abovementioned meaning, can be carried out in accordance with synthesis route C.

In step 1 of synthesis route C, the epoxide (X) is nucleophilically opened using the substituted cyclohexylalkanol (VIII). If an asymmetrically substituted epoxide is used in the reaction, the resulting alcohol (XI) can be obtained as a mixture of two regioisomers. This reaction can, for example, be carried out with the addition of 0.02% (mol) to 20% (mol), preferably 0.5% (mol) to 10% (mol), of a Lewis acid; preferred Lewis acids contain a boron atom; $BF_3$—$OEt_2$ is particularly preferred. The resulting alcohol (XI) is esterified by methods well known to those skilled in the art. Here, the esterification can take place by heating the alcohol (XI) and the corresponding carboxylic acid in a water separator in the presence of an entraining agent (for example, toluene or cyclohexane) with the addition of 0.01% (mol) to 10% (mol), preferably 0.1% (mol) to 5% (mol) of an acid, preferably p-toluenesulphonic acid or sulphuric acid, or by reaction of the alcohol (XI) with the corresponding carboxylic acid anhydride in the presence of triethylamine and 0.5% (mol) to 50% (mol), preferably, 1.0% (mol) to 30% (mol), 4-dimethylaminopyridine.

The following equations can illustrate the methods according to the invention:

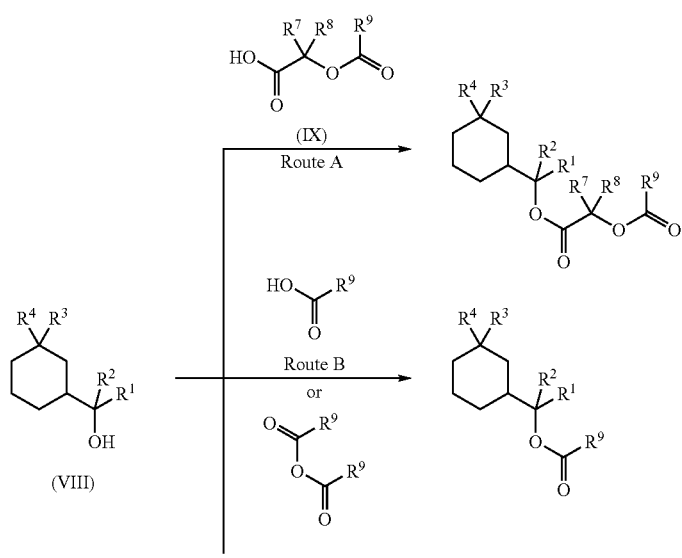

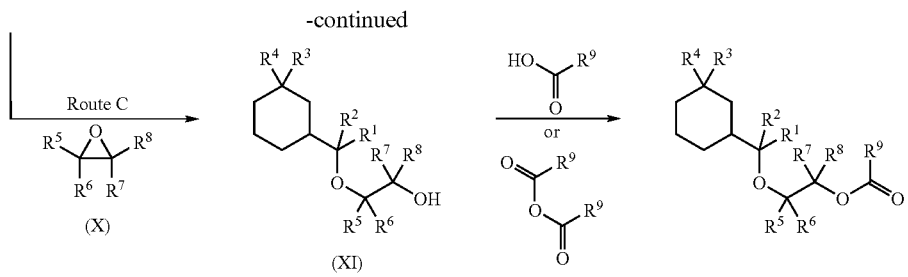

Alternatively, the alicyclic esters of the formula (I), according to the invention, in which $R^1$ and $R^2$—independently of one another—are $CH_3$ or $CH_2CH_3$, $R^3$ and $R^4$—independently of one another—are H or $CH_3$, $R^5$ and $R^6$ together are oxygen and $Y=\text{—}CR^7R^8OCOR^9$, where $R^7$, $R^8$ and $R^9$ have the above-mentioned meaning, can be prepared in accordance with synthesis route D.

In step 1 of synthesis route D, the substituted cyclohexylalkanol (VIII) is esterified by methods well known to those skilled in the art. Here, the esterification can be carried out by heating the substituted cyclohexylalkanol (VIII) and the corresponding carboxylic acid, where X is an OH group or a halogen, preferably, an OH group or a chlorine atom, in a water separator in the presence of an entraining agent (for example, toluene or cyclohexane) with the addition of 0.01% (mol) to 10% (mol), preferably 0.1% (mol) to 5% (mol), of an acid, preferably p-toluenesulphonic acid or sulphuric acid. Furthermore, the reaction of the substituted cyclohexylalkanol (VIII) with the corresponding carboxylic acid anhydride, where X is an OH group or a halogen, preferably, an OH group or a chlorine atom, can take place in pyridine.

In step 2, if X=OH, the ester (XII) is esterified with the corresponding carboxylic acid (Z=H). The reaction can be carried out, for example, in a water separator in the presence of an entraining agent (for example, toluene or cyclohexane) with the addition of 0.01% (mol) to 10% (mol), preferably, 0.1% (mol) to 5% (mol), of an acid. Preferred acids are p-toluenesulphonic acid or sulphuric acid. Furthermore, the reaction of the ester (XII) where X=OH with the corresponding carboxylic acid anhydride (Z=—C(O)R$^9$) can take place in the presence of triethylamine and 0.5% (mol) to 50% (mol), preferably 1.0% (mol) to 30% (mol), 4-dimethylaminopyridine.

If X=halogen, and, preferably, X=chlorine, the ester (XII) can, on the one hand, be reacted with an alkali metal salt of a carboxylic acid (Z=alkali metal; sodium and potassium are preferred) in the presence of an alkali metal salt, preferably, sodium bromide, or in the presence of the corresponding carboxylic acid anhydride. On the other hand, the ester (XII) where X=halogen and, preferably, X=chlorine can be reacted with a carboxylic acid (Z=H) in the presence of a base, preferably, potassium carbonate.

Route D:

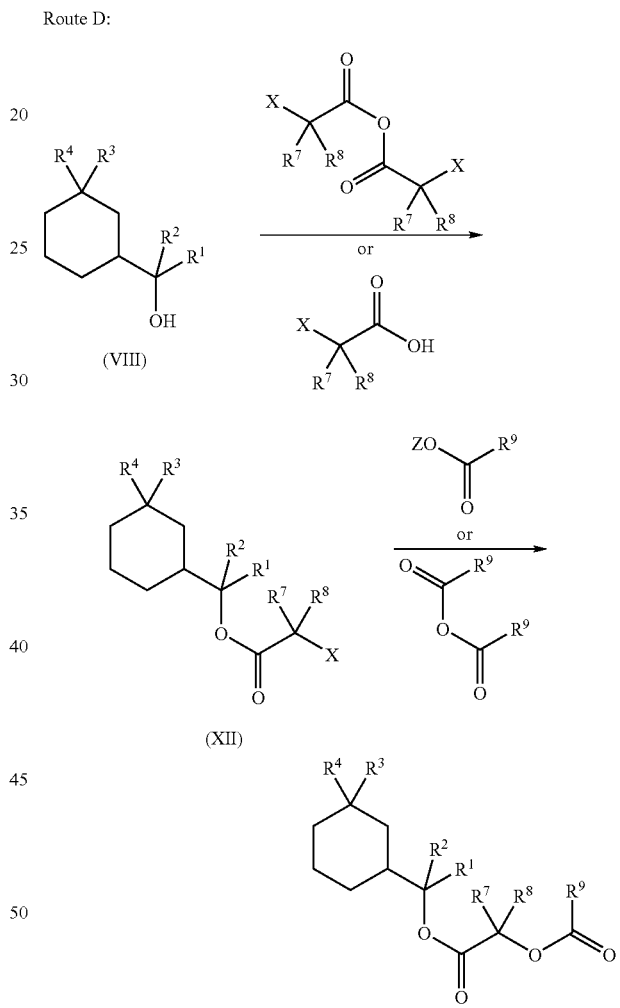

The following examples illustrate the invention:

EXAMPLE 1

2-(1-cyclohexylethoxy)-2-methylpropyl propionate 2-(1-cyclohexylethoxy)-2-methyl-1-propanol: $BF_3$—$OEt_2$ (2.0 ml) is added dropwise to a solution of 1-cyclohexylethanol (16.6 g, 127.0 mmol) and isobutylene oxide (2.9 g, 40.0 mmol) in cyclohexane (20 ml) that has been cooled to 0° C. The reaction mixture is now stirred at 0° C. for a further 30 minutes, and further, $BF_3$—$OEt_2$ (2.0 ml) is then added. After a further 3 hours at 0° C., the cooling is removed and the reaction solution is washed once with 1 M NaOH (15 ml). The organic phase is dried over $Na_2SO_4$, filtered off and freed from solvent in a rotary evaporator. The 1-cyclohexylethanol that has not completely reacted is removed from the crude product; thus, obtained by means of bulb tube distillation (BTD) and 5.3 g crude 2-(1-cyclohexylethoxy)-2-methyl-1-propanol is obtained which has a GC content of 75% and can be used in the next reaction without further purification.

2-(1-cyclohexylethoxy)-2-methylpropyl propionate: triethylamine (1.6 g, 15 mmol) and 4-dimethylaminopyridine (0.13 g, 1.0 mmol) are added successively to a solution of 2-(1-cyclohexylethoxy)-2-methyl-1-propanol (GC purity: 75%; crude product from the first stage) (1.46 g, 5.5 mmol) and propionic anhydride (2.0 g, 15 mmol). After stirring for 1 hour at room temperature, the reaction solution is diluted with ether (100 ml), and the organic phase is washed twice with 2 M HCl and twice with saturated $NaHCO_3$ solution. The combined organic phases are dried over $Na_2SO_4$, filtered off, and freed from solvent in a rotary evaporator. After flash chromatography (cyclohexane/EtOAc=45:1, $R_f$=0.25) and bulb tube distillation (BTD: 137° C., 0.5 mbar), 930 mg (70%) 2-(1-cyclohexylethoxy)-2-methylpropyl propionate is obtained as a colorless oil.

Odour: strongly musk, erogenous, ambergris-tinged, flowery $^1$H-NMR (200 MHz, $CDCl_3$): δ (ppm)=0.80–1.35 (m, 6H), 1.06 (d, J=6.1 Hz, 3H), 1.16 (t, J=7.5 Hz, 3H), 1.18 (s, 6H), 1.55–1.85 (m, 5H), 2.37 (q, J=7.5 Hz, 2H), 3.40 (quin, J=6.1 Hz, 1H), 3.95 (s, 2H).

$^{13}$C-NMR (50 MHz, $CDCl_3$): δ (ppm)=9.1, 19.7, 23.8, 24.0, 26.5, 26.6, 26.7, 27.7, 28.5, 29.5, 44.9, 70.3, 71.6, 73.7, and 174.3.

The following compounds of Examples 2 and 3 were prepared analogously to the methods described under Example 1, except that the esterification was carried out with acetic anhydride (Example 2) or isobutyric anhydride (Example 3). Thus, only the spectroscopic data are given at this point:

EXAMPLE 2

2-(1-cyclohexylethoxy)-2-methylpropyl acetate

Odour: musk, flowery, and fruity.
BTD: 140° C., 0.6 mbar.
$^1$H-NMR (200 MHz, $CDCl_3$): δ (ppm)=0.80–1.35 (m, 6H), 1.06 (d, J=6.2 Hz, 3H), 1.18 (s, 6H), 1.56–1.88 (m, 5H), 2.08 (s, 3H), 3.40 (quin, J=6.2 Hz, 1H), 3.92 (d, J=11.2 Hz, 1H), and 3.95 (d, J=11.2 Hz, 1H).
$^{13}$C-NMR (50 MHz, $CDCl_3$): δ (ppm)=19.7, 20.9, 23.7, 24.0, 26.4, 26.5, 26.6, 28.4, 29.4, 44.8, 70.4, 71.6, 73.6, and 170.8.

EXAMPLE 3

2-(1-cyclohexylethoxy)-2-methylpropyl isobutyrate

Odour: musk, erogenous, and flowery.
BTD: 164° C., 0.5 mbar.
$^1$H-NMR (200 MHz, $CDCl_3$): δ (ppm)=0.80–1.30 (m, 6H), 1.06 (d, J=6.2 Hz, 3H), 1.18 (s, 6H), 1.19 (d, J=7.0 Hz, 6H), 1.60–1.90 (m, 5H), 2.58 (hep, J=7.0 Hz, 1H), 3.40 (quin, J=6.2 Hz, 1H), and 3.93 (s, 2H).
$^{13}$C-NMR (50 MHz, $CDCl_3$): δ (ppm)=18.9 (2C), 19.7, 23.7, 24.0, 26.4, 26.5, 26.6, 28.4, 29.4, 34.1, 44.8, 70.1, 71.6, 73.7, and 176.7.

The following compounds of Examples 4 and 5 were prepared analogously to the methods described under Example 1, except that the alcohol component used was 1-cyclohexyl-1-propanol, which can be prepared from cyclohexylmagnesium chloride and propanal by a Grignard reaction, instead of 1-cyclohexyl-1-ethanol. The esterification was carried out with acetic anhydride (Example 4) or propionic anhydride (Example 5). Thus, only the spectroscopic data are given at this point:

EXAMPLE 4

2-(1-cyclohexylpropoxy)-2-methylpropyl acetate

Odour: weakly musk, flowery, and fruity.
BTD: 161° C., 0.75 mbar.
$^1$H-NMR (200 MHz, $CDCl_3$): δ (ppm)=0.80–1.30 (m, 6H), 0.86 (t, J=7.4 Hz, 3H), 1.19 (s, 6H), 1.35–1.50 (m, 2H), 1.55–1.80 (m, 5H), 2.08 (s, 3H), 3.24 (q, J=5.4 Hz, 1H), and 3.95 (s, 2H).
$^{13}$C-NMR (50 MHz, $CDCl_3$): δ (ppm)=9.5, 20.9, 24.0, 24.1, 24.7, 26.6 (2C), 26.7, 28.5, 29.2, 41.5, 70.8, 73.5, 76.7, and 170.9.

EXAMPLE 5

2-(1-cyclohexylpropoxy)-2-methylpropyl propionate

Odour: musk, flowery, and fruity.
BTD: 155° C., 0.55 mbar.
$^1$H-NMR (200 MHz, $CDCl_3$): δ (ppm)=0.86 (t, 7.4 Hz, 3H), 0.90–1.25 (m, 6H), 1.16 (t, J=7.6 Hz, 3H), 1.18 (s, 6H), 1.30–1.55 (m, 2H), 1.55–1.85 (m, 5H), 2.36 (q, J=7.6 Hz, 2H), 3.24 (q, J=5.3 Hz, 1H), and 3.94 (s, 2H).
$^{13}$C-NMR (50 MHz, $CDCl_3$): δ (ppm)=9.1, 9.5, 24.0, 24.1, 24.7, 26.6 (2C), 26.7, 27.7, 28.6, 29.2, 41.5, 70.6, 73.7, 76.7, and 174.2.

The following compounds of Examples 6 and 7 were prepared analogously to the methods described under Example 1, except that the alcohol component used was 2-cyclohexyl-2-propanol, which can be prepared from cyclohexylmagnesium chloride and acetone by a Grignard reaction, instead of 1-cyclohexyl-1-ethanol. Furthermore, propylene oxide was used instead of isobutylene oxide. The esterification was carried out with acetic anhydride (Example 6) or propionic anhydride (Example 7). Thus, only the spectroscopic data are given at this point:

EXAMPLE 6

2-(1-cyclohexyl-1-methylethoxy) propyl acetate/2-(1-cyclohexyl-1-methylethoxy)-1-methylethyl acetate Regioisomer ratio=1:3
Odour: weakly musk, and fruity.
BTD: 142° C., 0.6 mbar.
The spectroscopic data relate to the main isomer:
$^1$H-NMR (200 MHz, $CDCl_3$): δ (ppm)=0.9–1.25 (m, 6H), 1.06 (s, 6H), 1.22 (d, J=6.4 Hz, 3H), 1.70–1.85 (m, 5H), 2.03 (s, 3H), 3.28 (dd, J=9.7, 5.0 Hz, 1H), 3.37 (dd, J=9.7, 5.8 Hz, 1H), 5.00 (ddq, J=5.0, 5.8, 6.4 Hz, 1H).
$^{13}$C-NMR (50 MHz, $CDCl_3$): δ (ppm)=16.9, 21.3, 22.5, 22.7, 26.7, 26.8, 26.9, 27.4, 27.5, 46.4, 63.4, 70.3, 78.0, and 170.6.

EXAMPLE 7

2-(1-cyclohexyl-1-methylethoxy) propyl propionate/ 2-(1-cyclohexyl-1-methylethoxy)-1-methylethyl propionate Regioisomer ratio=1:3
Odour: musk, and fruity.
BTD: 152° C., 0.72 mbar.
The spectroscopic data relate to the main isomer:
$^1$H-NMR (200 MHz, CDCl$_3$): δ (ppm)=0.88–1.24 (m, 6H), 1.06 (s, 6H), 1.13 (t, J=7.6 Hz, 3H), 1.23 (d, J=6.4 Hz, 3H), 1.70–1.85 (m, 5H), 2.30 (q, J=7.6 Hz, 2H), 3.28 (dd, J=9.6, 5.1 Hz, 1H), 3.37 (dd, J=9.6, 5.9 Hz, 1H), and 4.97 (ddq, J=5.1, 5.9, 6.4 Hz, 1H).
$^{13}$C-NMR (50 MHz, CDCl$_3$): δ (ppm)=9.2, 17.0, 22.5, 22.7, 26.7, 26.8, 26.9, 27.4, 27.5, 27.9, 46.5, 63.5, 70.1, 77.0, and 174.1.

The following compounds of Examples 8 and 9 were prepared analogously to the methods described under Example 1, except that the alcohol component used was 1-(3-methyl-cyclohexyl)-ethanol, which can be prepared by hydrogenation of 3-methylacetophenone, instead of 1-cyclohexyl-1-ethanol. The esterification was carried out with acetic anhydride (Example 8) or propionic anhydride (Example 9). Thus, only the spectroscopic data are given at this point:

EXAMPLE 8

2-[1-(3-methyl-cyclohexyl)-ethoxy]-2-methylpropyl acetate

Odour: musk, flowery, and fruity.
BTD: 142° C., 0.75 mbar.
$^1$H-NMR (200 MHz, CDCl$_3$): δ (ppm)=0.55 (q, J=12.1 Hz, 1H), 0.72–0.86 (m, 1H), 0.88 (d, J=6.6 Hz, 3H), 1.07 (d, J=6.1 Hz, 3H), 1.18 (s, 6H), 1.20–1.40 (m, 4H), 1.60–1.82 (m, 4H), 2.08 (s, 3H), 3.40 (quin, J=6.1 Hz, 1H), and 3.95 (d, J=11.2 Hz, 2H).
$^{13}$C-NMR (50 MHz, CDCl$_3$): δ (ppm): 19.7, 20.9, 23.1, 23.8, 24.0, 26.2, 28.0, 32.7, 35.3, 35.4, 44.9, 70.5, 71.6, 73.7, and 170.9.

EXAMPLE 9

2-[1-(3-methyl-cyclohexyl)-ethoxy]-2-methylpropyl propionate

Odour: strongly musk, flowery, and fruity.
BTD: 153° C., 0.75 mbar.
$^1$H-NMR (200 MHz, CDCl$_3$): δ (ppm)=0.55 (q, J=12.1 Hz, 1H), 0.72–0.86 (m, 1H), 0.88 (d, J=6.6 Hz, 3H), 1.07 (d, J=6.1 Hz, 3H), 1.16 (t, J=7.6 Hz, 3H), 1.18 (s, 6H), 1.20–1.40 (m, 4H), 1.60–1.82 (m, 4H), 2.37 (q, J=7.6 Hz, 2H), 3.40 (quin, J=6.1 Hz, 1H), and 3.94 (d, J=11.2 Hz, 2H).
$^{13}$C-NMR (50 MHz, CDCl$_3$): δ (Ppm): 9.1, 19.7, 23.0, 23.8, 24.1, 26.3, 27.7, 29.0, 32.7, 35.4, 37.1, 44.9, 70.3, 71.6, 73.8, and 174.2.

EXAMPLE 10A

2-[1-(3,3-dimethylcyclohexyl)-1-methylethoxy]-2-oxoethyl propionate (Propionyloxy) acetic acid: a solution consisting of propionyl chloride (64.7 g, 0.7 mol) and hydroxyacetic acid (19.0 g, 0.25 mol) is heated at 40° C., until the hydroxyacetic acid has completely dissolved. The excess propionyl chloride is then distilled off and 35.6 g of crude product containing 82% of (propionyloxy)acetic acid is obtained as a colorless liquid. The crude product can be used in the subsequent reaction without further purification.

2-[1-(3,3-dimethylcyclohexyl)-1-methylethoxy]-2-oxoethyl propionate: 4-dimethyl-aminopyridine (122 mg, 1.0 mmol) and 2-(3,3-dimethylcyclohexyl)-2-propanol (2.6 g, 15 mmol), [which is obtainable from methylmagnesium chloride and 1-(3,3-dimethylcyclohexyl)-ethanone by a Grignard reaction] are added successively to a solution of 81% (propionyloxy) acetic acid (2.7 g, 16.5 mmol) in CH$_2$Cl$_2$ (15 ml). The reaction solution is now cooled to 0° C. and dicyclohexylcarbodiimide (3.4 g, 16.5 mmol), dissolved in CH$_2$Cl$_2$ (5 ml) is added. After 1 h at 0° C., the cooling is removed, and the reaction mixture is stirred for a further 16 h at room temperature. The precipitate that has precipitated is, then, filtered off, and the filtrate is freed from solvent in a rotary evaporator. The resulting crude product is taken up in n-pentane (20 ml) and the precipitate that forms is again filtered off. The filtrate is also washed twice with 0.5 M HCl and twice with saturated NaHCO$_3$ solution, and the organic phase is then dried over Na$_2$SO$_4$, filtered off, and concentrated in a rotary evaporator. After purification by flash chromatography (cyclohexane/EtOAc=10:1, R$_f$=0.23) and subsequent bulb tube distillation (BTD: 221° C., 1.3 mbar), 3.1 g (73%) 2-[1-(3,3-dimethylcyclohexyl)-1-methylethoxy]-2-oxoethyl propionate is obtained as a colorless liquid.

Odour: strongly musk, woody, and erogenous.
$^1$H-NMR (200 MHz, CDCl$_3$): δ (ppm)=0.80–1.40 (m, 4H), 0.88 (s, 3H), 0.92 (s, 3H), 1.18 (t, J=7.6 Hz, 3H), 1.42 (d, J=0.6 Hz, 6H), 1.50–1.76 (m, 4H), 2.03 (tt, J=12.4, 3.1 Hz, 1H), 2.44 (q, J=7.6 Hz, 2H), 4.46 (d, J=15.8 Hz, 1H), and 4.55 (d, J=15.8 Hz, 1H).
$^{13}$C-NMR (50 MHz, CDCl$_3$): δ (ppm)=8.9, 22.2, 23.3 (2C), 24.5, 27.0, 27.1, 30.7, 33.6, 39.0, 40.0, 42.0, 61.0, 87.4, 166.7, and 173.5.

EXAMPLE 10B

Alternatively to the methods in Example 10a, 2-[1-(3,3-dimethylcyclohexyl)-1-methylethoxy]-2-oxoethyl propionate can be prepared via the following two-stage synthesis route.

1-(3,3-dimethylcyclohexyl)-1-methylethyl chloroacetate: chloroacetic anhydride (213.7 g, 1.12 mol) is added in portions to a solution of 2-(3,3-dimethylcyclohexyl)-2-propanol (127.7 g, 0.75 mol) in pyridine (175 ml), which has been cooled to 0° C., in such a way that the temperature does not rise above 10° C. When the addition is complete, the reaction mixture is allowed to allowed to warm to room temperature and stirred for a further 3 hours. The reaction mixture is then cooled to 0° C. again and water (500 ml) is added. The phases are separated, and the aqueous phase is extracted a further three times with ether (500 ml). The combined organic phases are also washed twice with 1 M HCl, then dried, filtered off and freed from solvent in a rotary evaporator. Subsequent distillation (b.p. 103° C., 0.5 mbar) yields 152 g (82%) 1-(3,3-dimethylcyclohexyl)-1-methylethyl chloroacetate as a colorless liquid.

2-[1-(3,3-dimethylcyclohexyl)-1-methylethoxy]-2-oxoethyl propionate: K$_2$CO$_3$ (6.2 g, 45 mmol) and 1-(3,3-dimethylcyclohexyl)-1-methylethyl chloroacetate (2,5 g, 10 mmol) are added successively to a solution of propionic acid (1.8 g, 30 mmol) in acetone (20 ml). After the suspension has been heated under reflux for 36 hours, it is allowed to cool and ether (80 ml) and 10% $K_2CO_3$ solution (50 ml) are added. After phase separation has taken place, the aqueous phase is freed from residual acetone and the aqueous phase is also extracted twice with 50 ml diethyl ether. The combined organic phases are also washed once with water and once with saturated NaCl solution, then dried, filtered off and freed from solvent in a rotary evaporator. After purification by flash chromatography (cyclohexane/EtOAc=10:1, $R_f$=0.23) and subsequent bulb tube distillation, (BTD: 215° C., 0.9 mbar) 2.1 g (78%) 2-[1-(3,3-dimethylcyclohexyl)-1-methylethoxy]-2-oxoethyl propionate is obtained as a colorless liquid.

The odor and the spectroscopic data are identical to the data for the compound that was prepared under Example 10a.

The following compounds were prepared analogously to the methods described under Example 8a (sic), except that in Example 9 (sic) acetyloxyacetic acid (which can be prepared from hydroxyacetic acid and acetyl chloride), in Example 10 (sic) isobutyryloxyacetic acid, (which can be prepared from hydroxyacetic acid and isobutyryl chloride) and in Example 11 (sic) butyryloxyacetic acid, (which can be prepared from hydroxyacetic acid and butyryl chloride) is used in the esterification. Thus, only the spectroscopic data are given at this point:

EXAMPLE 11

2-[1-(3,3-dimethylcyclohexyl)-1-methylethoxy]-2-oxoethyl acetate

Odour: strongly musk, woody, and animal.
BTD: 192° C., 0.35 mbar.
$^1$H-NMR (200 MHz, $CDCl_3$): δ (ppm)=0.80–1.08 (m, 3H), 0.88 (s, 3H), 0.92 (s, 3H), 1.30–1.45 (m, 3H), 1.42 (s, 3H), 1.43 (s, 3H), 1.50–1.72 (m, 2H), 2.03 (tt, J=12.5, 3.1 Hz, 1H), 2.15 (s, 3H), 4.47 (d, J=15.7 Hz, 1H), and 4.52 (d, J=15.7 Hz, 1H).
$^{13}$C-NMR (50 MHz, $CDCl_3$): δ (ppm)=20.5, 22.2, 23.3, 23.4, 24.6, 27.0, 30.7, 33.7, 39.0, 40.1, 42.1, 61.1, 87.6, 166.8, and 170.3.

EXAMPLE 12

2-[1-(3,3-dimethylcyclohexyl)-1-methylethoxy]-2-oxoethyl isobutyrate

Odour: musk, ambergris-tinged, and woody.
BTD: 261° C., 0.66 mbar.
$^1$H-NMR (200 MHz, $CDCl_3$): δ (ppm)=0.80–1.12 (m, 3H), 0.88 (s, 3H), 0.92 (s, 3H), 1.22 (d, J=7.0 Hz, 6H), 1.28–1.45 (m, 3H), 1.41 (s, 3H), 1.42 (s, 3H), 1.50–1.75 (m, 2H), 2.05 (tt, J=12.4, 3.1 Hz, 1H), 2.65 (hep, J=7.0 Hz, 1H), 4.46 (d, J=15.8 Hz, 1H), and 4.54 (d, J=15.8 Hz, 1H).
$^{13}$C-NMR (50 MHz, $CDCl_3$): δ (ppm)=18.8 (2C), 22.2, 23.3, 23.4, 24.5, 27.0, 30.7, 33.6, 33.7, 39.0, 40.0, 41.9, 60.9, 87.3, 166.7, and 176.1.

EXAMPLE 13

2-[1-(3,3-dimethylcyclohexyl)-1-methylethoxy]-2-oxoethyl butyrate

Odour: weakly musk, and woody.
BTD: 274° C., 0.81 mbar.
$^1$H-NMR (200 MHz, $CDCl_3$): δ (ppm)=0.80–1.12 (m, 3H), 0.88 (s, 3H), 0.92 (s, 3H), 0.98 (t, J=7,4 Hz, 3H), 1.28–1.45 (m, 3H), 1.41 (s, 3H), 1.42 (s, 3H), 1.50–1.75 (m, 2H), 1.70 (sex, J=7,4 Hz, 2H), 2.04 (tt, J=12.4, 3.1 Hz, 1H), 2.39 (t, J=7.4 Hz, 2H), 4.46 (d, J=15.6 Hz, 1H), and 4.54 (d, J=15.6 Hz, 1H).
$^{13}$C-NMR (50 MHz, $CDCl_3$): δ (ppm)=13.6, 18.2, 22.2, 23.3 (2C), 24.5, 27.0, 30.7, 33.6, 35.7, 39.0, 40.0, 42.0, 60.9, 87.4, 166.7, and 172.7.

The following compounds were prepared analogously to the methods described under Example 10a, except that the alcohol component used was 2-cyclohexyl-2-propanol, which can be prepared from cyclohexylmagnesium chloride and acetone by a Grignard reaction, instead of 2-(3,3-dimethylcyclohexyl)-2-propanol. Acetyloxyacetic acid, (which can be prepared from hydroxyacetic acid and acetyl chloride, Example 14) and propionyloxyacetic acid, (which can be prepared from hydroxyacetic acid and propionyl chloride, Example 15) were used in the esterification. Thus, only the spectroscopic data are given at this point:

EXAMPLE 14

2-(1-cyclohexyl)-1-methylethoxy)-2-oxoethyl acetate

Odour: weakly musk, and woody.
BTD: 200° C., 1.3 mbar.
$^1$H-NMR (200 MHz, $CDCl_3$): δ (ppm)=0.90–1.35 (m, 5H), 1.43 (s, 6H), 1.62–1.95 (m, 6H), 2.15 (s, 3H), and 4.50 (s, 2H).
$^{13}$C-NMR (50 MHz, $CDCl_3$): δ (ppm)=20.4, 23.3 (2C), 26.5, (3C), 27.2 (2C), 46.4, 61.0, 87.5, 166.6, and 170.1.

EXAMPLE 15

2-(1-cyclohexyl)-1-methylethoxy)-2-oxoethyl propionate

Odour: weakly musk, and woody.
BTD: 210° C., 1.2 mbar.
$^1$H-NMR (200 MHz, $CDCl_3$): δ (ppm)=0.90–1.37 (m, 5H), 1.18 (t, J=7,5 Hz, 3H), 1.43 (s, 6H), 1.62–1.95 (m, 6H), 2.44 (q, J=7,5 Hz, 2H), and 4.50 (s, 2H).
$^{13}$C-NMR (50 MHz, $CDCl_3$): δ (ppm)=8.9, 23.3 (2C), 26.4, (3C), 27.1, 27.2 (2C), 46.5, 61.0, 87.5, 166.7, and 173.5.

EXAMPLE 16

1-cyclohexyl-1-methylethyl acetate

Triethylamine (4.6 g, 45 mmol) and 4-dimethylaminopyridine (0.40 g, 3.3 mmol) are added successively to a solution of 2-cyclohexyl-2-propanol (2.1 g, 15.0 mmol), [which is obtainable from cyclohexylmagnesium chloride and acetone by a Grignard reaction] and acetic anhydride (4.6 g, 45 mmol). After stirring for 1 hour at room temperature, the reaction solution is diluted with ether (200 ml), and the organic phase is washed twice with 2 M HCl and twice with $NaHCO_3$ solution. The combined organic phases are dried over $Na_2SO_4$, filtered off and freed from solvent in a rotary evaporator. After flash chromatography (cyclohexane/EtOAc=20:1, $R_f$=0.24) and bulb tube distillation (BTD:

120° C., 0.3 mbar) 2.3 g (83%) 1-cyclohexyl-1-methylethyl acetate is obtained as a colorless oil.

Odour: weakly musk, and woody.

$^1$H-NMR (200 MHz, CDCl$_3$): δ (ppm)=0.90–1.35 (m, 6H), 1.38 (s, 6H), 1.61–1.92 (m, 5H), and 1.97 (s, 3H).

$^{13}$C-NMR (50 MHz, CDCl$_3$): δ (ppm)=22.4, 23.3 (2C), 26.5 (3C), 27.3 (2C), 46.1, 85.2, and 170.2.

The following compound in Example 17 was prepared analogously to the method described under Example 16, except that propionic anhydride was used in the esterification. Thus, only the spectroscopic data are given at this point:

EXAMPLE 17

1-cyclohexyl-1-methylethyl propionate

Odour: weakly musk, and woody.

BTD: 125° C., 0.25 mbar.

$^1$H-NMR (200 MHz, CDCl$_3$): δ (ppm)=0.89–1.36 (m, 6H), 1.09 (t, J=7.5 Hz, 3H), 1.39 (s, 6H), 1.61–1.96 (m, 5H), and 2.24 (q, J=7.5 Hz, 2H).

$^{13}$C-NMR (50 MHz, CDCl$_3$): δ (ppm)=9.3, 23.4 (2C), 26.6 (3C), 27.3 (2C), 28.8, 46.3, 84.8, and 173.6.

The following compounds were prepared analogously to the method described in Example 16, except that the alcohol component used was 2-(3,3-dimethylcyclohexyl)-2-propanol, [which can be prepared from methylmagnesium chloride and 1-(3,3-dimethylcyclohexyl)-ethanone by a Grignard reaction] instead of 2-cyclohexyl-2-propanol. The esterification was carried out with acetic anhydride (Example 18) or propionic anhydride (Example 19). Thus, only the spectroscopic data are indicated at this point:

EXAMPLE 18

1-(3,3-dimethylcyclohexyl)-1-methylethyl acetate

Odour: musk, and woody.

BTD: 125° C., 0.17 mbar.

$^1$H-NMR (200 MHz, CDCl$_3$): δ (ppm)=0.8–1.12 (m, 4H), 0.88 (s, 3H), 0.92 (s, 3H), 1.22–1.42 (m, 4H), 1.38 (s, 3H), 1.39 (s, 3H), 1.62–1.76 (m, 1H), and 1.97 (s, 3H).

$^{13}$C-NMR (50 MHz, CDCl$_3$): δ (ppm)=22.3, 22.4, 23.3, 23.4, 24.6, 27.0, 30.7, 33.7, 39.1, 40.1, 41.6, 84.9, and 170.1.

EXAMPLE 19

1-(3,3-dimethylcyclohexyl)-1-methylethyl propionate

Odour: musk, and woody.

BTD: 128° C., 0.11 mbar.

$^1$H-NMR (200 MHz, CDCl$_3$): δ (ppm)=0.8–1.13 (m, 4H), 0.88 (s, 3H), 0.91 (s, 3H), 1.09 (t, J=7.5 Hz, 3H), 1.22–1.42 (m, 4H), 1.38 (s, 3H), 1.39 (s, 3H), 1.58–1.76 (m, 1H), and 2.24 (q, J=7.5 Hz, 2H).

$^{13}$C-NMR (50 MHz, CDCl$_3$): δ (ppm)=9.3, 22.4, 23.3, 23.4, 24.6, 27.0, 28.8, 30.7, 33.7, 39.1, 40.2, 41.8, 84.6, and 173.4.

EXAMPLE 20

The present perfume oil can be used to perfume diverse cosmetic products.

Composition:

| Ingredients | Parts by weight |
| --- | --- |
| 1. Citrophoral base (H&R) | 5.0 |
| 2. Aldehyde C10, 10% in BA | 5.0 |
| 3. Aldehyde C11 MOA, 10% in BA | 3.0 |
| 4. Farenal (H&R) | 3.0 |
| 5. Aldehyde C11, 10% in IPM | 5.0 |
| 6. Citroxal, 50% in DEP | 2.0 |
| 7. trans-Hex-2-enol, 10% in BA | 2.0 |
| 8. Vertocitral (H&R) | 1.0 |
| 9. Linalyl acetate | 45.0 |
| 10. Citrylal (H&R) | 5.0 |
| 11. Mandarinal (Firmenich) | 4.0 |
| 12. Lilial (Givaudan Roure) | 75.0 |
| 13. Lyral (IFF) | 75.0 |
| 14. Profarnesol (H&R) | 5.0 |
| 15. Nerolidol | 5.0 |
| 16. Linalool | 45.0 |
| 17. African geranium oil | 5.0 |
| 18. Phenylethyl alcohol | 75.0 |
| 19. Geraniol | 15.0 |
| 20. Nerol | 10.0 |
| 21. Hexylcinnamaldehyde alpha | 50.0 |
| 22. Methyl dihydrojasmonate | 15.0 |
| 23. Benzyl salicylate | 100.0 |
| 24. trans,cis-2-Nonadienol, 0.1% in IPM | 5.0 |
| 25. Allylionone (Givaudan Roure) | 3.0 |
| 26. Isomethylionone gamma | 75.0 |
| 27. Eugenol | 7.0 |
| 28. Cedryl acetate | 40.0 |
| 29. Sandolen (H&R) | 5.0 |
| 30. Citral | 5.0 |

BA = benzyl alcohol;
IPM = isopropyl myristate;
DEP = diethyl phthalate

The addition of 355 parts by weight 2-(1-cyclohexylethoxy)-2-methylpropyl propionate (1000 parts by weight in total) leads to a clearly discernible harmonisation of the rose-like flowery heartnote. In addition, the fine erogenous musk note imparts an exceptional aura and increased bonding to the present composition. In this context, the valuable character of 2-(1-cyclohexylethoxy)-2-methylpropyl propionate, in particular, comes into its own compared with compositions containing conventional musk fragrances.

55 parts by weight 2-[1-(3,3-dimethylcyclohexyl)-1-methylethoxy]-2-oxoethyl propionate (700 parts by weight in total) imparts a woody, musk note to the composition that is not achieved with existing musk fragrances. Furthermore, the entire composition, gains in fullness and appears more valuable.

What is claimed is:

1. A compound of the formula (I)

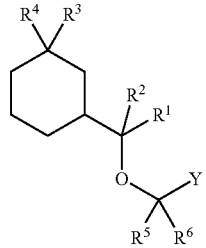

(I)

where
a) $R^1$=CH$_3$, $R^3$=H or CH$_3$ and $R^2$ and $R^4$=H,
$R^5$ and $R^6$—independently of one another—are H or CH$_3$ and
Y=—CR$^7$R$^8$OCOR$^9$, where R$^7$ and R$^8$—independently of one another—are H or CH$_3$ and
R$^9$ is a branched or straight-chain C$_1$ to C$_5$ alkyl group or a branched or straight-chain C$_2$ to C$_5$ alkylene group, or
b) $R^1$ and $R^2$—independently of one another—are CH$_3$ or CH$_2$CH$_3$,
$R^3$ and $R^4$—independently of one another—are H or CH$_3$,
$R^5$ and $R^6$ together are oxygen and
Y=—CR$^7$R$^8$OCOR$^9$, where R$^7$, R$^8$ and R$^9$ have the abovementioned meaning, or
$R^1$ and $R^2$—independently of one another—are CH$_3$ or CH$_2$CH$_3$,
$R^3$ is H or CH$_3$,
$R^4$ is CH$_3$,
$R^5$ and $R^6$ together are oxygen, and
Y=R$^9$, where R$^9$ has the above meaning, or
c) $R^1$ and $R^2$—independently of one another—are CH$_3$ or CH$_2$CH$_3$,
$R^3$, $R^4$, $R^5$ and $R^6$—independently of one another—are H or CH$_3$ and
Y=—CR$^7$R$^8$OCOR$^9$, where R$^7$, R$^8$ and R$^9$ have the abovementioned meaning.

2. The compound according to claim 1 of the formula (IV)

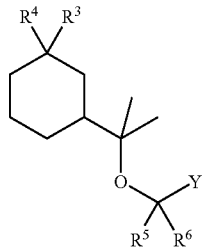

(IV)

where
$R^3$ and $R^4$—independently of one another—are H or CH$_3$,
$R^5$ and $R^6$ together are oxygen, and
Y=—CR$^7$R$^8$OCOR$^9$, where R$^7$, R$^8$ and R$^9$ have the meaning given in claim 1 or
$R^3$ is H or CH$_3$,
$R^4$ is CH$_3$,
$R^5$ and $R^6$ together are oxygen, and
Y=R$^9$, where R$^9$ has the meaning given in claim 1.

3. The compound according to claim 1 of the formula (VI)

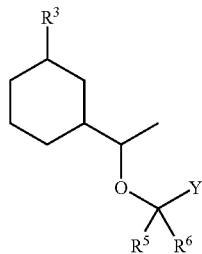

(VI)

where
$R^3$=H or CH$_3$,
$R^5$ and $R^6$—independently of one another—are H or CH$_3$, and
Y=—CR$^7$R$^8$OCOR$^9$, where R$^7$, R$^8$ and R$^9$ have the meaning given in claim 1.

4. The compound according to claim 1, wherein said compound is 2-(1-cyclohexylethoxy)-2-methylpropyl propionate, 2-[1-(3,3-dimethylcyclohexyl)-1-methylethoxy]-2-oxoethyl propionate or 2-[1-(3,3-dimethylcyclohexyl)-1-methylethoxy]-2-oxoethyl acetate.

5. A method for the preparation of the compound according to claim 1 by reacting a substituted cyclohexylalkanol of the formula

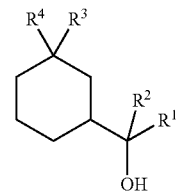

with
a) carboxylic acids of the formula

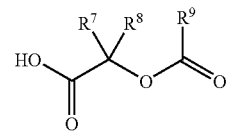

where
$R^1$ and $R^2$—independently of one another—are CH$_3$ or CH$_2$CH$_3$,
$R^3$ and $R^4$—independently of one another—are H or CH$_3$,
$R^5$ and $R^6$ together are hydrogen and
Y=—CR$^7$R$^8$OCOR$^9$ where R$^7$, R$^8$ and R$^9$ have the meaning given in claim 1, or
b) carboxylic acids R$^9$—COOH or carboxylic anhydrides (R$^9$—CO)$_2$O where
$R^1$ and $R^2$—independently of one another—are CH$_3$ or CH$_2$CH$_3$,
$R^3$ and $R^4$—independently of one another—are H or CH$_3$,
$R^5$ and $R^6$ together are oxygen, and
Y=—CR$^7$R$^8$OCOR$^9$, where R$^7$, R$^8$ and R$^9$ have the above mentioned meaning, or $R^1$ and $R^2$—independently of one another—are $CH_3$ or $CH_2CH_3$,
$R^3$ is H or $CH_3$,
$R^4$ is $CH_3$,
$R^5$ and $R^6$ together are oxygen, and
$Y=R^9$, where $R^9$ has the above meaning, or c) epoxides of the formula

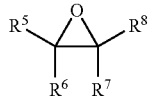

where
$R^1=CH_3$, $R^3$=H or $CH_3$ and $R^2$ and $R^4$=H,
$R^5$ and $R^6$—independently of one another—are H or $CH_3$ and
$Y$=—$CR^7R^8OCOR^9$, where $R^7$, $R^8$ and $R^9$ have the abovementioned meaning, or
$R^1$ and $R^2$—independently of one another—are $CH_3$ or $CH_2CH_3$,
$R^3$, $R^4$, $R^5$ and $R^6$—independently of one another—are H or $CH_3$, and
$Y$=—$CR^7R^8OCOR^9$, where $R^7$, $R^8$ and $R^9$ have the meaning given in claim 1, or d) a carboxylic acid $XCR^7R^8$—COOH or a carboxylic anhydride $(XCR^7R^8$—$CO)_2O$ in a first step and with $R^9$—COOZ or $(R^9$—$CO)_2O$ in a second step where
$R^1$ and $R^2$—independently of one another—are $CH_3$ or $CH_2CH_3$,
$R^3$ and $R^4$—independently of one another—are H or $CH_3$,
$R^5$ and $R^6$ together are oxygen, and
$Y$=—$CR^7R^8$ $OCOR^9$, where $R^7$, $R^8$ and $R^9$ have the meaning given in claim 1,
X=halogen or OH,
Z=alkali metal or H.

6. A fragrance mixture comprising one or more compounds according to claim 1 and a carrier.

7. A perfumed product comprising one or more compounds according to claim 1 and a carrier.

8. The compound according to claim 2 wherein $R^4$=methyl.

9. The compound according to claim 2 wherein $R^9$=methyl, ethyl or n-propyl.

10. The compound according to claim 3 wherein $R^5$ and $R^6$=methyl.

11. The compound according to claim 3 wherein $R^9$=methyl, ethyl or n-propyl.

* * * * *

UNITED STATES PATENT AND TRADEMARK OFFICE
CERTIFICATE OF CORRECTION

PATENT NO. : 7,064,102 B2  
APPLICATION NO. : 10/510024  
DATED : June 20, 2006  
INVENTOR(S) : Marcus Eh It is certified that error appears in the above-identified patent and that said Letters Patent is hereby corrected as shown below:

Title page, Attorney, Agent, or Firm, replace "Stephen" with --Stephan--

Column 2, line 65, replace "C," with --$C_1$--

Column 5, line 63, replace "famesene" with --farnesene--

Column 6, line 50, replace "cirtonellal" with --citronellal--

Column 6, line 57, replace "bomeol" with --borneol--

Column 18, line 53, replace "is allowed to allowed to" with --is allowed to--

Signed and Sealed this

Twenty-sixth Day of August, 2008

JON W. DUDAS  
*Director of the United States Patent and Trademark Office*